United States Patent [19]

White

[11] Patent Number: 5,300,651

[45] Date of Patent: Apr. 5, 1994

[54] PROTECTED DERIVATIVES OF TRYPTOPHAN, PROCESSES FOR THEIR PREPARATION AND THEIR USE FOR THE PREPARATION OF DIPEPTIDE, POLYPEPTIDE OR PROTEIN STRUCTURES

[75] Inventor: Peter D. White, Southwell, United Kingdom

[73] Assignee: Calbiochem-Novabiochem AG, Laufelfingen, Switzerland

[21] Appl. No.: 888,667

[22] Filed: May 27, 1992

[30] Foreign Application Priority Data

May 31, 1991 [CH] Switzerland .................. 1613/91

[51] Int. Cl.$^5$ .................. C07F 9/06; C07D 209/18
[52] U.S. Cl. .................. 548/113; 548/454; 548/495; 530/333; 530/337
[58] Field of Search .................. 548/495, 113, 454

[56] References Cited

FOREIGN PATENT DOCUMENTS 0376218 7/1990 European Pat. Off. ........... 548/495

OTHER PUBLICATIONS

Tetrahedron, (Incl. Tetrahedron Reports), vol. 44 No. 3, 1 Mar. 1988, Oxford GB, pp. 843–857 E. Atherton et al.
"Peptide Synthesis, Part 10. Use of Pentafluorophenyl esters of Flourenyl Methoxycarbonylamino Acids in Solid Phase Peptide Synthesis".
Journal of The American Chemical Society, vol. 94, No. 8, 19 Apr. 1972, Gaston, Pa. US pp. 2855–2859, D. Yamashiro et al.
"The Use of N-alpha, N-im bis (Tert-butyloxycarbonyl)histidine and n-alpha-2-(p-biphenyly)isopropyloxycarbonyl-N-im-tertbutyloxcarbonylhistidine in the solid-phase synthesis of histidine-containing peptides".
Chemical Abstracts, vol. 115, No. 19, 11 Nov. 1990, Abstract No. 208510S, H. Kalbacher et al.
"Acid labile protection of histidine and arginine in spps using adpoc derivatives" & Pept. 1990, Proc, Eur. Pept. Symp. 21st 1990 Leiden.
Tetrahedron Letters, vol. 28, No. 48, pp. 6031–6034, 1987, Sieber et al. "Protection of Histidine In Peptide Synthesis: A Reassessment of the Trityl Group".
Chem. Soc. Chem. Commun., 1984, Frazen et al., Synthesis, Properties, and Use of $N^{in}$-Boc-tryptophan Derivatives, pp. 1699–1700.

Primary Examiner—Mary C. Lee
Assistant Examiner—Joseph K. McKane
Attorney, Agent, or Firm—Seidel, Gonda, Lavorgna & Monaco

[57] ABSTRACT

A derivative of tryptophan is provided wherein the NH-group of the tryptophan indole nucleus is protected with tert.-butyloxycarbonyl (BOC) and the α-amino group is protected by 9-fluorenyl-methyloxy-carbonyl (FMOC). The carboxylic acid group of the tryptophan derivative may comprise a free COOH group, may be modified with a protecting or activating group, or may comprise an acyl group bonded to another chemical moiety, such as a polymer, another amino acid, a dipeptide, a polypeptide, or a protein. The tryptophan derivative is useful in the preparation of dipeptides, polypeptides or proteins containing at least one tryptophan-derived amino acid residue.

7 Claims, No Drawings

PROTECTED DERIVATIVES OF TRYPTOPHAN, PROCESSES FOR THEIR PREPARATION AND THEIR USE FOR THE PREPARATION OF DIPEPTIDE, POLYPEPTIDE OR PROTEIN STRUCTURES

BACKGROUND OF THE INVENTION

It is well known in the art that the NH-group of the indole nucleus of the amino acid tryptophan is liable to an attack of several reagents if said NH-group is present as free, not protected NH-group. The problems are specially severe if the synthesis of a dipeptide, polypeptide or protein has to be performed which comprises in its amino acid sequence at least one moiety of tryptophan and furthermore at least one moiety of arginine which has its guanidino group protected. Even if the guanidino-protecting group is split off using extremely mild conditions, the yields of the corresponding dipeptide, polypeptide or protein are lowered due to an attack at the NH-group of the indole nucleus of the tryptophan.

Until now several protective groups for the NH of the indole nucleus of tryptophan in combination with several protective groups for the alphaamino group of tryptophan were used in order to avoid the above stated difficulties. However, until now no combination of protective groups for the indole nucleus with protective groups for the alphaamino groups were found out which on the one hand result in corresponding protected derivatives which have the necessary stability and which can be used for the performance of the synthesis of dipeptides, polypeptides and proteins in which synthesis no drastical lowerings of the yield are observed in the reaction step where sidechain protective groups of other amino acids of the amino acids sequence are split off.

It was the aim of the present invention to provide new protected derivatives of tryptophan which do not have the disadvantages of the until now used protected derivatives.

DESCRIPTION OF THE PRIOR ART

In the publication of E. Atherton et al. in Tetrahedron, (incl. Tetrahedron Reports), volume 44, no. 3, 1988, pages 843–857, there is described the use of pentafluorophenyl esters of amino acids which have the alphaamino group protected with the 9-fluorenylmethyloxy-carbonyl group, which in the following will be abbreviated as Fmoc. In said publication there is also described a histidine derivative in which the NH-group of the imidazole nucleus of histidine is protected with the tert.-butyloxycarbonyl group, which in the following will be abbreviated as Boc. Accordingly, in said publication there is described the protected histidine derivative Fmoc-His (Boc)-pentafluorophenyl ester (see page 850, line 7 from the bottom of said publication). The protected amino acid derivatives described in said publication are used in the solid phase peptide synthesis and in said publication there is furthermore mentioned the performance of the synthesis of a peptide chain which comprises in its amino acid sequence a moiety of histidine and a moiety of tryptophan as well. The used tryptophan derivative has its alphaamino group protected with Fmoc, the amino group of the indole nucleus however is not protected, and on page 849, lines 3 to 10, there is explained that when the corresponding peptide is cleaved from the resin on which the synthesis was performed, only a yield of 37% of the crude peptide is obtained, due to a readdition of the intermediate benzyl cation to the indole nucleus of the tryptophan moiety which is present in the corresponding amino acid sequence. The electrophilic attack at the free NH-group of the indole nucleus of the corresponding tryptophan moiety is furthermore illustrated through the formula (7) on page 850 of said publication.

In the publication of E. Sieber et al. in Tetrahedron Letters, vol. 28, no. 46, pages 6031–6034, 1987, there are described protected histidine derivatives in which the alphaamino group of histine is protected with Fmoc and the NH-group of the imidazole nucleus of the histine is protected with trityl. In said publication also corresponding histine derivatives were tested in which the NH-group of the imidazole nucleus is protected with other protective groups, including Boc, and it was observed that said protected histidine derivatives are unstable, specially if they come into contact with nucleophiles (see page 6031, lines 5, 6 and 7 of the first paragraph).

In the publication of D. Yamashiro et al. in the Journal of the American Chemical Society, volume 94, no. 8, 1972, pages 2855–2859, there are as well described protected histidine derivatives in which the imidazole nucleus of the histidine is protected with Boc, and in which the alphaamino group of the histidine is either protected with Boc or protected with the (p-biphenylyl) isopropyl-oxycarbonyl-group. The corresponding protected histidine derivatives are used for preparing peptide chains, including one in which one of the amino acids of said sequence is arginine in which the guanidino group of the arginine is protected with a nitro group. The histidine derivatives in which the NH-group of the imidazole nucleus is protected with Boc, however, are not sufficiently stable (see the explanations given above).

In the publication of H. Franzén et al. in J. Chem. Soc., Chem. Commun., 1984, pages 1699 and 1700, there is described the methylester of tryptophan in which the alphaamino group as well as the NH-group of the indole nucleus are protected with Boc. In said publication there is also described the conversion of the correspondingly protected methyl ester of tryptophan into the hydrazide, and it is explained that from the protected methyl ester the two Boc-protective groups can be split off by a short treatment with trifluoroacetic acid, while the ester group of said methyl ester is not split through said treatment. In said publication there is furthermore described that a treatment of said tryptophan methyl esters, in which the alphaamino group as well as the NH-group of the indole nucleus is protected with Boc, with a 2.7-molar hydrochloric acid in dioxane at room temperature results in a selective splitting off of the alphaamino protective group while surprisingly the NH-group of the indole nucleus remains in its protected form with the Boc group. The yield in said procedure for the selective cleavage of the alphaamino protective group was 60%, if however the reaction time was longer or if higher concentrations of hydrochloric acid were used, then also the Boc-protective group of the indole nucleus was split off.

In said publication also the conversion of a corresponding tryptophan methyl ester in which the NH-group of the indole nucleus is protected with Boc, and the alphaamino group is present in its free form into a dipeptide according to the procedure of active esters is described. Specifically in the reaction scheme illustrated on page 1699, there is bonded to the free alphaamino group of the tryptophan derivative a phenyl alaline which has its alphaamino group protected with Boc. Finally, said dipeptide is converted to a tripeptide by bonding a leucine methyl ester to the C- end of said dipeptide, i.e. the carboxylic acid group of the tryptophan moiety. Then the Boc-protective group of the alphaamino group of the phenyl alaline of said tripeptide was split off selectively, and to the resulting free amino group of the phenyl alaline moiety, there was coupled according to the azide coupling reaction, the hydrazide of a further tryptophan moiety which is protected on its alphaamino group and on its indole nucleus with Boc to yield a corresponding tetrapeptide. In said publication, however, the splitting off of the protective groups of said tretrapeptide is not described.

In an annotation at the bottom of page 1699 of said publication, there is remarked that preliminary experiments indicate that the corresponding methyl esters having the indole nucleus and the alphaamino group of tryptophan protected with Boc, i.e. the protected tryptophan derivative Boc-Trp($N^{in}$-Boc)-OMe was partially destroyed by catalytic hydrogenation over a palladium catalyst.

It was the aim of the present invention to provide new protected derivatives of tryptophan which can be used in the solid phase synthesis of dipeptides, polypeptides and proteins, and which do not have the above stated disadvantages of the until now known protected tryptophan derivatives. Specially the new tryptophan derivatives should be stable, when submitted to a hydrogenating treatment, and they should be furthermore stable when protein chains are synthesized, in which there are present further amino acid moieties having protected side chains, specially moieties of arginine having a protected guanidino group, for instance a guanidino group protected with a sulfonyl containing protective group.

SUMMARY OF THE INVENTION

It was now surprisingly found out that a new tryptophan derivative in which the indole nucleus is protected with Boc and the alphaamino group of the tryptophan is protected with Fmoc, is stable when submitted to a hydrogenation. This property was quite unexpected, keeping in mind that corresponding tryptophan derivatives in which the alphaamino protective group is as well Boc, are partially destroyed by a catalytic hydrogenation.

Contrary to the histidine derivatives of an analogous structure, i.e. histidine derivatives in which the imidazole nucleus of the histine is protected with Boc and the alphaamino group of the histidine is protected with Fmoc, which histidine derivatives do not have the necessary stability towards nucleophiles, the new inventive tryptophane derivatives have said desired stability.

DESCRIPTION OF THE INVENTION

One object of the invention is a new protected derivative of tryptophan wherein the NH-group of the indole nucleus is protected with the tert.-butyloxycarbonyl group (Boc) and the alphaamino group of the tryptophan is protected with the 9-fluorenyl-methyloxycarbonyl group (Fmoc), and wherein the carboxylic acid group of said tryptophan derivative is present as free COOH group, in a protected form or an activated form or bonded as corresponding acyl group to the remaining part of a molecule.

It is advantageous that in the new inventive tryptophan derivatives the Boc-protective group of the NH-group of the indole nucleus is split off under acidic conditions while the Fmoc-protective group of the alphaamino group of the tryptophan is split off under basic reaction conditions.

In the inventive protected derivatives of tryptophan, accordingly, the carboxylic acid group according to one embodiment of the invention, is present as free COOH group.

According to a further preferred embodiment of the present invention, the carboxylic acid group of the inventive protected tryptophan derivative is bonded as acyl group to a polymeric material and/or is bonded as acyl group to the amino group of a further amino acid of a dipeptide structure or a polypeptide structure or a protein structure.

According to a specially preferred embodiment of the present invention, the carboxylic acid group of the inventive tryptophan derivative is bonded directly to a resin or via a linker to a resin. According to another preferred embodiment of the present invention, the carboxylic acid group of the inventive tryptophan derivative is bonded as acyl group to the alphaamino group of a further amino acid of a dipeptide structure, polypeptide structure or protein structure in which amino acid sequence of the dipeptide, polypeptide or protein there is optionally present at least one amino acid moiety of the amino acid arginine or of an arginine which is protected on its guanidino group.

In the present specification the term "polypeptide" should comprise polypeptides which are built up of three, four, five or more amino acid moieties, and accordingly the definition "dipeptide structure, polypeptide structure or protein structure" is intended to comprise any desired amino acid sequence comprising at least two amino acid moieties in which amino acid sequence the corresponding amino acids are optionally protected in their side chains.

If the acyl group of the inventive protected tryptophan derivative is bonded to such a dipeptide structure, polypeptide structure or protein structure which comprises in its amino acid sequence at least one moiety of a arginine which is protected on its guanidino group then a preferred protective group of said guanidino group is a corresponding group which comprises in its structure a sulfonyl group. Preferred examples for sulfonyl containing protective groups or the guanidino groups of the arginine moiety are the methoxy-trimethyl-sulphonyl protective group and the 2,2,5,7,8-pentamethyl-chroman-6-sulphonyl protective group.

According to a further embodiment of the present invention, in the inventive protected derivatives of tryptophan the carboxylic acid group is present in an activated form, and a preferred example of an activated carboxylic acid group is one which is activated as benzo-triazole-1-yl-oxy-tris-pyrrolidinophosphonium-hexafluorophosphate.

A further object of the present invention is a process for the preparation of a protected derivative of tryptophan in which the NH-group of the indole nucleus is protected with the tert.-butyloxycarbonyl group (Boc) and the alphaamino group of the tryptophan is protected with the 9-fluorenyl-methyloxy-carbonyl group (Fmoc) and wherein the carboxylic acid group of the protected tryptophan derivative is present as free carboxylic acid group or as activated carboxylic acid group, in which process in a first reaction step tryptophan which has a protected carboxylic acid group or a salt thereof, is protected at its alphaamino group and wherein in a second reaction step the NH-group of the indole nucleus is protected through the introduction of the Boc-protective group and wherein in a third reaction step the group which protects the alphaamino group and the group which protects the carboxylic group, are split off, preferably simultaneously split off while the Boc-protective group remains on the indole nucleus wherein in a fourth reaction step the alphaamino group of the tryptophan is protected with the Fmoc protective group and the tryptophan derivative having a free carboxylic acid group is isolated or the carboxylic acid group of said protected tryptophan derivative is activated.

According to a preferred embodiment of said process, in the first reaction step there is used a tryptophan derivative which has its carboxylic acid group protected in the form of the benzyl ester or a salt of said benzyl ester. A preferred salt which is used as starting material is the salt of the benzyl ester of said tryptophan derivative with hydrochloric acid.

A preferred protective group of the alphaamino group, which is introduced in the first reaction step of said process, is the benzyloxy-carbonyl-protective group. Said preferred protective group is advantageously introduced by reacting the benzyl ester or the salt thereof with a carbobenzyloxy-hydroxy-succinimide-ester.

The first reaction step of said process is preferably performed in a solvent, and furthermore preferably performed in the presence of a base. A preferred solvent used in said first reaction step is acetonitrile, and a preferred base which is present is an amine, specially preferred a tertiary amine. A preferred example for such a tertiary amine is diisopropyl-ethylamine.

In the second reaction step the Boc protective group is introduced in order to protect the NH-group of the indole nucleus. Said introduction of the protective group Boc is preferably performed by reacting the intermediate product of the first reaction step with an anhydride which corresponds to the formula

$(Boc)_2O$.

Said reaction of the intermediate product of the first reaction step with the reagent which introduces the protective group Boc into the indole nucleus, is preferably performed in the presence of a solvent, and preferably also in the presence of a base. Preferred solvents are organic solvents, and specially preferred is acetonitrile. As base, amines are preferred, and specially preferred tertiary amines. A preferred example of a tertiary amine which can be present when the second reaction step is performed, is the 4-dimethyl-aminopyridine.

In the third reaction step of said process, from the intermediate product which is obtained after the first reaction step, the group which protects the carboxylic acid group of the tryptophan, which is preferably a benzyl ester, and the group which protects the alphaamino group of the tryptophan, which is preferably a benzyloxycarbonyl-protective group, are split off, and specially preferred both said protective groups are split off simultaneously. The above mentioned preferred protective groups are preferably split off simultaneously in the third reaction step by submitting the product of the second reaction step to a hydrogenating treatment. Said hydrogenating treatment is preferably performed in the presence of a noble metal catalyst and in the presence of a solvent, either by bubbling hydrogen gas through the reaction medium or by adding to said reaction medium an ethylenically unsaturated compound. A preferred noble metal of said catalyst which is present during said hydrogenating treatment is a corresponding palladium catalyst, and specially preferred is a 5% palladium on carbon.

As already mentioned above, said hydrogenating treatment can be either performed by bubbling hydrogen gas through the reaction medium or by adding an ethylenically unsaturated compound, and a preferred ethylenically unsaturated compound which is added is the 1-4-cyclohexadiene. The preferred solvent which is present during said hydrogenating treatment is a lower aliphatic alcohol, preferably methanol or ethanol. If the hydrogenating treatment is performed by bubbling hydrogen gas through the reaction medium in the presence of the noble metal catalyst, a specially preferred lower aliphatic alcohol which is used as solvent, is methanol, while if the hydrogenating treatment is performed by adding in the presence of the noble metal catalyst the ethylenically unsaturated compound, like e.g. 1,4-cyclohexadiene, the preferred solvent is the lower aliphatic alcohol ethanol.

Before the new inventive protected derivatives of tryptophan were prepared, there were already synthesized protected tryptophan derivatives in which the NH-group of the indole is protected with Boc, and the alphaamino group of indole is as well protected with Boc, while the carboxylic acid group is present in the form of the methyl ester. Said protected derivatives of the tryptophan, however, were degradated in an essential amount if they were submitted to a catalytic hydrogenation in the presence of a palladium catalyst (see the before mentioned publication of Franzén). It, accordingly, was completely unexpected that the intermediate product of the present process which has as well the NH-group of the indole nucleus of the tryptophan protected with Boc, while however the alphaamino group is protected with benzyloxy-carbonyl, can be submitted to a hydrogenating treatment in the presence of a palladium catalyst which is either performed by bubbling hydrogen gas through the reaction medium or by adding an ethylenically unsaturated compound without partial degradation of the correspondingly protected tryptophan derivative. The third reaction step, accordingly, yields as intermediate product such a tryptophan derivative which has a free alphaamino group and a free carboxylic acid group, in which, however, the indole nucleus of the tryptophan is protected with Boc. Said intermediate product which is by-and-by formed during the hydrogenating or reductive treatment, is as well stable in the presence of the noble metal catalyst.

In the fourth reaction step of the inventive process said reaction product of the third reaction step which is a tryptophan derivative in which the alphaamino group and the carboxylic acid group are present in the free form, while the NH-group of the indole nucleus is protected with Boc, is then converted into a corresponding reaction product in which the free alphaamino group is protected with Fmoc. Said introduction of the Fmoc-protective group is preferably performed by reacting the product of the third reaction step with the 9-fluorenyl-methyloxycarbonyl-hydroxy-succinimide. Said fourth reaction step is preferably performed in the presence of a solvent, and specially preferred also in the presence of a base. A preferred solvent which is used in said fourth reaction step is acetonitrile or dioxane, and a preferred base which is added during said fourth reaction step, is an aqueous solution of an alkali metal carbonate, for example a 10% aqueous solution of sodium carbonate.

A further object of the present invention is a process for the preparation of a protected tryptophan derivative in which the alphaamino group is protected with Fmoc, the NH-group of the indole nucleus protected with Boc, and the carboxylic acid group is present in the free form or in an activated form. Said process is performed by using as starting material a tryptophan derivative which has a free carboxylic acid group and a free alphaamino group and by protecting in said tryptophan derivative the free alphaamino group and thereafter the free carboxylic acid group and by performing thereafter the second reaction step, the third reaction step and the fourth reaction step of the process described above. In said process the free alphaamino group of the tryptophan derivative is preferably protected through the introduction of a benzyloxycarbonyl protective group, for example by reacting said starting material with carbobenzyloxy-chloride. Furthermore, a free carboxylic acid group of said intermediate product is thereafter protected, preferably as a benzyl ester. This can, e.g. be done, by reacting the intermediate product with benzyl bromide. Then, after the introduction of the benzyloxycarbonyl protective group and the benzyl ester protective group, the reaction step 2, the reaction step 3, and the reaction step 4 of the inventive process described above can be performed.

The new inventive tryptophan derivatives in which the NH-group of the indole nucleus is protected with Boc, and the alphaamino group is protected with Fmoc, are very advantageous for performing the synthesis of dipeptide or polypeptide structures or protein structures, because during the corresponding synthesis there are formed intermediate products which are highly stable. A further advantage of the new inventive protected derivatives of tryptophan is that the Fmoc-protective group of the alphaamino group is split off under reaction conditions which are clearly different from the reaction conditions under which the Boc-protective group of the NH-group of the indole nucleus is split off.

A further object of the present invention, accordingly, is the use of the new inventive tryptophan derivative, in which the NH-group of the indole nucleus is protected with Boc, and the alphaamino group of the tryptophan is protected with Fmoc, while the carboxylic acid group of the tryptophan derivative is present in free form, in protected form, in activated form or bonded as acyl group to the remaining part of a molecule for preparing dipeptides or polypeptides or proteins, which have in their structure at least one tryptophan moiety which is protected on its indole nucleus with Boc.

Until now, usually the formyl-protective group and the 2,2,2-trichloroethoxy-carbonyl-protective group were used for protecting the NH-group of the indole nucleus of tryptophan during the performance of the synthesis of dipeptides, polypeptides and proteins. The above mentioned protective groups, however, have the disadvantage if compared with the Boc-protective group which is used in the inventive tryptophan derivatives for the protection of the NH-group of the indole nucleus, that the above stated protective groups used according to the prior art, are split off in an alkaline environment while the Boc-protective group which is present in the inventive protected tryptophan derivative is not split off if it comes into contact with solutions having a pH-value in the alkaline range. During the performance of the synthesis of peptides, it is frequently necessary to adjust the pH-value in the alkaline range.

According to the prior art, also the benzyloxycarbonyl-group was used in order to protect the NH-group of the indole nucleus of tryptophan. When the corresponding synthesis of the dipeptide, polypeptide or protein is finished, however, said benzyloxycarbonyl-protective group has to be split off under severe reaction conditions and, accordingly, sensitive peptide structures are often destroyed under said severe conditions.

Contrary to this, the Boc-protective group which is used for protecting the NH-group of the indole nucleus of the inventive tryptophan derivatives (in which furthermore the alphaamino group of the tryptophan is protected with Fmoc) can be split off under mild reaction conditions, for instance using trifluoroacetic acid, when the synthesis of the dipeptide, polypeptide or protein is finished. Under said mild reaction conditions no degradation of sensitive dipeptides, polypeptide structures and protein structures is observed.

A further advantage of the new inventive protected tryptophan derivatives is that the Boc-protective group which protects the NH-group of the indole nucleus of the tryptophan provides an excellent protection against an electrophilic attack, which optionally can occur during the performance of the synthesis of the dipeptide, polypeptide or protein. A corresponding electrophilic attack is usually to be observed if other protective groups which are present in the sequence of amino acids of the polypeptide or protein, like for instance side chain protecting groups, have to be removed, i.e. split off in the course of the peptide synthesis or protein synthesis, for instance at the end of said synthesis.

Keeping in mind that a corresponding histidine derivative in which the NH-protective group of a heterocyclic imidazole ring is Boc, and the group which protects the alphaamino group of histidine, is Fmoc, does not have the necessary stability, specially towards an attack of nucleophiles, it was completely unexpected that the new protected tryptophan derivatives according to the present invention which have an analogous pattern of protective groups, have the unexpected advantageous properties, specially an excellent stability towards nucleophiles and electrophiles.

An outstanding advantage of the new protected tryptophan derivatives, according to the present invention, is that the Boc-protective group which protects the NH-group of the indole nucleus, provides an excellent protection against an attack through electrophiles which can occur during the course of the synthesis of a polypeptide or a protein. Such an attack is often to be observed when in the course of the synthesis of the polypeptide or protein, other protective groups which are present in the amino acid sequence, have to be split off, for instance side chain protective groups.

In recent times, the side chain of the amino acid moiety arginine, i.e. the guanidino group of arginine, is frequently protected using corresponding protective groups which have in their structure a sulfonyl group. If such sulfonyl-containing protective groups are later on split off, then usually the yield of the recovered polypeptide or protein is lowered drastically because the indole nucleus of the at least one tryptophan moiety which is present in said dipeptide structure, polypeptide structure or protein structure, is sulfonated during the splitting off of the sulfonyl group containing protective groups of the arginine moiety. The corresponding problems of a sulfonation of the indole nucleus of one or more tryptophan moieties which are present in the polypeptide structure or protein structure, is to be observed not only if the indole nucleus of the tryptophan is not protected, i.e. the free NH-group of the indole nucleus is present, but the stated problems as to the sulfonation are also to be observed if the indole nucleus of the tryptophan is protected with one of the before mentioned protective groups which until now were used for protecting the indole nucleus of said amino acid moiety.

According to a preferred embodiment of the inventive use, accordingly, the new intentive derivatives of tryptophan are used for the preparation of such dipeptides, polypeptides or proteins which have in their amino acid sequence at least one group of a protected arginine. Preferably the guanidino group of the at least one moiety of arginine which is present in the amino acid sequence, is protected with such a protective group which has in its structure a sulfonyl group. Preferred sulfonyl containing protective groups of the guanidino group of the arginine are the methoxytrimethyl-sulfonyl-group which is usually abbreviated as Mtr, or the 2,2,5,7,8-pentamethyl-chroman-6-sulfonyl-protective group which is usually abbreviated as Pmc-group.

When the new inventive protected derivative of tryptophan in which the NH-group of the indole nucleus is protected with Boc, and the alphaamino group of the tryptophan is protected with Fmoc, is used for preparing a depeptide structure, a polypeptide structure or a protein structure, then the free COOH-group of said tryptophan derivative or a corresponding activated COOH-group can be coupled to the alphaamino group of a further amino acid moiety, which amino acid moiety is optionally the N-terminal of a polypeptide or protein. Thereafter the Fmoc-group which protects the alphaamino group of the tryptophan moiety can be split off yielding a corresponding free alphaamino group of the tryptophan moiety, while the indole nucleus remains protected with Boc. Optionally to said N-terminal tryptophan moiety there can be coupled a further amino acid moiety with its free COOH-group or activated COOH-group.

When the complete polypeptide chain or protein chain is synthesized, then the Boc-protective group which protects the NH-group of the indole nucleus of the at least one tryptophan moiety which is present in the corresponding polypeptide chain or protein chain, can be split off yielding the corresponding tryptophan moiety in which the NH-group of the indole nucleus is present as free unprotected NH-group.

According to preferred performance of the inventive use, accordingly, after the preparation of the amino acid sequence of the dipeptide, the polypeptide or the protein structure which comprises at least one moiety of a protected tryptophan derivative wherein the NH-group of the indole nucleus of the at least one tryptophan moiety is protected with Boc, said protective group is split off from the indole nucleus yielding a corresponding dipeptide, polypeptide or protein chain in which the NH-group of the indole nucleus of the at least one tryptophan moiety is present as free, unprotected NH-group.

A special advantage of the new inventive derivatives of tryptophan is that the Boc-protective group of the indole nucleus can be split off easily under acidic conditions, preferably by using trifluoroacetic acid in order to cleave said Boc-group. Accordingly, no essential loss of yield of the desired final product is to be observed when said indole protective group is split off.

It was found out that when the Boc-protective group is split off from the indole nucleus of the correspondingly protected tryptophan derivative, there is formed an unstable COOH-derivative of said heterocyclic NH-group. If thereafter the reaction product is further treated or isolated maintaining a mild basic reaction medium and low temperatures, then said unstable COOH-derivative is destroyed and the indole nucleus with the NH-group liberated.

If the Boc-protective group of the indole nucleus of the tryptophan moiety is split off from such a dipeptide, polypeptide or protein sequence which comprises in its amino acid sequence at least one moiety of an arginine which is protected at its guanidino group, then the Boc-protective group of the tryptophan moiety and the arginine protective group can be split off in a single reaction step. Preferably this simultaneous splitting off of the above stated protective groups can be performed using trifluoro-acetic acid.

If the guanidino protective group of the at least one arginine moiety which is present in the prepared dipeptide, polypeptide or protein structure is a guanidino protective group which comprises a sulfonyl group, then said protective group can be split off without any damage to the indole nucleus of the at least one tryptophan moiety which is as well present in the prepared dipeptide, polypeptide or protein structure. If the simultaneous splitting off of the guanidino protective group and the Boc-protective group of the indole nucleus is performed, then probably intermediately the unstable COOH-derivative of the NH-group of the indole nucleus is produced which protects the corresponding indole group from an attack through the sulfonyl containing protective group which is split off from the correspondingly protected arginine moiety. In any case, no electrophilic attack of any sulfonyl containing group to the NH-group of the indole nucleus was observed.

When the new inventive tryptophan derivatives are used for preparing a dipeptide, polypeptide or protein sequence which comprises in its amino acid sequence at least one moiety of an arginine which is protected at its guanidino group with a sulfonyl containing protective group, then a sulfonation of the indole nucleus of the tryptophan can be completely or nearly completely avoided if both said protective groups are split off using trifluoro-acidic acid. Contrary to this, a tryptophan moiety in which the NH of the indole nucleus is not protected or is protected with one of the protective groups which until now had been used for said purpose, the sulfonation of the indole nucleus during the splitting off of the guanidino protective group of the arginine moiety with trifluoro-acetic acid, amounts up to 40%.

While tryptophan moieties with an unprotected indole nucleus or an indole nucleus protected with protective groups which were until now used, result in high losses of yield in the reaction step where sulfonyl containing protective groups of the guanidino group of the arginine moiety are split off, the loss of yield in this case is usually only 5%, if the synthesis had been performed with the new inventive derivatives of tryptophan in which the protective group for the indole nucleus is Boc.

According to a preferred use of inventive products there is accordingly prepared a dipeptide, a polypeptide chain or a protein chain, which comprises at least one amino acid moiety which is tryptophan, and furthermore at least one amino acid moiety which is arginine and wherein the NH-group of the indole nucleus of the at least one tryptophan moiety is protected with Boc, and the guanidino group of the at least one arginine moiety is protected and wherein
either first the protective group of the arginine and thereafter the Boc-protective group of the tryptophan moiety is split off, or wherein
the protective group of the guanidino group of the arginine and the Boc of the tryptophan are split off simultaneously.

If furthermore the group which protects the guanidino group of the arginine comprises in its structure a sulfonyl group, the splitting off of the Boc-protective group of the tryptophan moiety and the splitting off of the sulfonyl containing protective group of the at least one arginine moiety are performed under acidid conditions.

Preferably the splitting off of the Boc-protective group of the at least one tryptophan moiety and the splitting off of the sulfonyl containing protective group of the at least one arginine moiety are performed using trifluoro-acetic acid.

The present invention now will be further illustrated with the following non-limitative examples. With said examples there is explained the preparation of an inventive tryptophan derivative in which the alphaamino protective group is Fmoc, the NH-protective group of the indole nucleus is Boc, and the carboxylic acid group is present as free COOH-group (see the examples 1 through 4).

Furthermore, through example 5, the use of the corresponding inventive tryptophan derivative for the preparation of a polypeptide is explained.

EXAMPLE 1

Preparation of an Intermediate Product in which the Alphaamino Group of the Tryptophan is Protected with the Carbobenzyloxy-Protective Group One equivalent of a tryptophan derivative in which the NH-group of the indole nucleus is present as free not protected NH-group, and in which the carboxylic acid group of the tryptophan is protected as benzylester, was dissolved in di-isopropyl-ethylamine and aceto-nitrile, and to said solution there was added one equivalent of the carbobenzyloxy-hydroxy-succinimide. Said mixture was stirred at a temperature of 0° C. for three hours and thereafter the aceto-nitrile was evaporated.

The residue which remained was dissolved in ethylacetate and the organic phase was washed with one molar aqueous hydrochloric acid, thereafter with one molar aqueous sodium bicarbonate solution, thereafter with water, and finally with a saturated sodium chloride solution. The organic layer was then dried over magnesium sulfate, filtered and concentrated by evaporation. There was obtained a crystalline product in which the carboxylic acid group is still protected as benzylester and the alphaamino group of the tryptophan is protected with the carbobenzyloxy-carbonyl group while the NH-group of the indole nucleus was present as free not protected NH-group. Said product was used without performing any further purification as starting material in example 2.

EXAMPLE 2

Introduction of the Boc-Protective Group in Order to Protect the NH-group of the Indole Nucleus One equivalent of the intermediate product which was prepared according to the process of example 1 was dissolved in aceto-nitrile. The tert.-butyloxycarbonyl-protective group, i.e. the Boc-protective group, was introduced using the corresponding anhydride having the following formula:

$(Boc)_2O$ and 1.1-equivalents of said anhydride and 0.1-equivalents of 4-dimethylamino-pyridine were added to the above stated solution and the mixture stirred at a temperature of 0° C. for one hour. After said reaction time of one hour, there was performed a high pressure liquid chromatography (hplc) which showed that the reaction was already about 80% complete. Thereafter, each hour 0.1-equivalents of the anhydride of the above stated formula were added to the reaction mixture, until the above stated test showed that the reaction was about 98% complete. Attention has to be paid that the presence of a too high excess of the anhydride of the above stated formula, during the reaction is avoided, because if the excess of the anhydride in the reaction mixture is too high, then possibly the mixed imide is formed.

As soon as the reaction has completed to about 98%, the solvent was evaporated and the remaining residue dissolved in diethyl-ether. Said organic solution then was washed with two-molar aqueous citric acid solution, thereafter one-molar aqueous sodium bicarbonate solution, thereafter with saturated sodium chloride solution, and finally with water. Then the organic phase was dried over magnesium sulfate and after the removal of the drying agent evaporated. There remained an oily product which had a purity of 94% (according to a corresponding test by hplc).

In said oily product, the NH-group of the indole nucleus was protected with the Boc-protective group, and the carboxylic acid group as well as the alphaamino group were protected with identical protective groups as in example 1. The corresponding product was used without any further purification as starting material in the following example 3.

EXAMPLE 3

Simultaneous Splitting Off of the Benzyloxycarbonyl-Protective Group from the Alphaamino Group and the Benzylester-Protective Group of the Carboxylic-Acid Group Said simultaneous splitting off of the above stated protective groups was performed according to two alternative procedures.

Procedure A

One equivalent of the intermediate product which was obtained according to example 2, was dissolved in methanol, and a hydrogenating catalyst was added, i.e. 5% of palladium on carbon. Said catalyst was added in an amount of 1 part by weight per 100 parts by weight of the starting material.

At room temperature, hydrogen gas was bubbled through said mixture for 12 hours. Thereafter the mixture was filtered through diatomaceous earth (the product which is available on the market with the trademark Celite) in order to remove the palladium on carbon catalyst, and the Celite was washed two times with methanol.

Thereafter the solvent was evaporated yielding a corresponding product in which the NH-group of the indole nucleus was protected with Boc, and in which the alphaamino group and the carboxylic acid group of the tryptophan were present in free, not protected form. Said product was used as starting material without any further purification procedures in example 4.

Procedure B

One equivalent of the product according to example 2 was dissolved in ethanol, and the 5% palladium on carbon catalyst was added in an amount of 1 part by weight of said catalyst per 100 parts by weight of the used starting material. Thereafter, two equivalents of 1,4-cyclohexadiene were added and the mixture was stirred for eight hours under nitrogen gas.

Thereafter the mixture was filtered through diatomaceous earth (the trademark product Celite) in order to remove the palladium on carbon catalyst, and the Celite was washed first with ethanol and thereafter with acetic acid. Corresponding tests showed that ethanol was the best of the tested solvents for the proton transfer which occurs during said reaction in the course of the hydrogenating cleavage. Said tests, however, showed that ethanol did not dissolve the final product very well and because of this after the washing step with ethanol there was performed the above stated further washing step of the Celite with acetic acid.

From the so recovered solution there were then evaporated the solvents, and the corresponding product in which the NH-group of the indole nucleus is protected with Boc, while the alphaamino group and the carboxylic acid group of the tryptophan are present in the free, not protected form, remained as white solid material. Said product was used without any further purification for performing the process according to the following example 4.

EXAMPLE 4

Protection of the Alphaamino Group with the Fmoc-Protective Group

One equivalent of the intermediate product which was obtained according to the preceding example 3 (either according to procedure A or according to procedure B) was dissolved in aceto-nitrile and two equivalents of a 10% aqueous solution of sodium carbonate were added. Upon the addition of said solution, the above stated starting material was precipitated from the mixed solution. Thereafter, one equivalent of the 9-fluorenyl-methyloxy-carbonyl-hydroxy-succinimide were added, and the mixture was stirred for eight hours at a temperature of 0° C. in order to introduce the Fmoc-protective group. After said reaction time, the performance of a high pressure liquid chromatography (hplc) demonstrated that in the corresponding reaction mixture there was no longer present any starting material. The corresponding solution, however, was nevertheless still turbid.

Thereafter, to said solution there was added a two-molar aqueous solution of citric acid until in the mixture a pH-value of about 3 was reached, and then the aqueous phase was extracted with diethyl-ether.

The organic phase was washed with a saturated aqueous sodium chloride solution and thereafter with water, and finally dried over magnesium sulfate. After the evaporation of the solvent, there remained the desired final product in the form of an off-white foam.

Through the performance of a high pressure liquid chromatography (hplc) it could be demonstrated that said product had a purity of 90%.

When the corresponding synthesis was performed in example 3, according to the procedure B, the total yield over all the reaction steps was 75% of the theoretical yield (accordingly calculated based on the starting material which was introduced in example 1).

If the corresponding synthesis was performed in example 3, according to procedure A, then the total yield over all the reaction steps was 60% of the theoretical yield (i.e. calculated based on the starting material which has been introduced into example 1).

EXAMPLE 5

Preparation of a Polypeptide Using the Inventive Protected Tryptophan Derivative of Example 4

The polypeptide of the following formula was prepared:

*Fmoc-Trp-Arg-Arg-Arg-Arg-Val-OH.*

In said polypeptide the used abbreviations have the following meaning:
Fmoc-Trp—a tryptophan which is protected on its alphaamino group with Fmoc (9-fluorenyl-methyloxycarbonyl),
Arg—means arginine,
Val-OH—is valine which has the free carboxylic acid group (C-terminal of the polypeptide sequence).

The polypeptide of the above stated amino acid sequence was prepared according to the solid phase method on a polystyrene resin with acryl amide residues on kieselguhr (diatomaceous earth). The first amino acid was bonded to said polystyrene resin via a linker (hydroxymethylphenoxy-acetic acid), and the first amino acid was protected on its alphaamino group with Fmoc, i.e. the 9-fluorenylmethyloxy-carbonyl group. The corresponding polystyrene resin to which there was bonded as first amino acid a valine moiety which is protected on its alphaamino group with Fmoc, accordingly, is illustrated through the following formula:

*Fmoc-Val-NovaSyn-KA-resin.*

The coupling of the following amino acids to the valine moiety of the above stated structure which is bonded to the resin, was performed by using the corresponding amino acids to be bonded, with the alphaamino group thereof, being protected with Fmoc, and the carboxylic acid group thereof activated with the benzotriazole-1-yl-oxy-tris-pyrrolidino-phosphoni-umhexafluorphosphate (abbreviated as PyBOP).

Per gram of the resin there were bonded 0.1 millimol of the valine which is protected on its alphaamino group, and the synthesis was started using one g of said resin of the above stated formula. To the resin there was bonded a 2.5-fold excess of the corresponding subsequent amino acid which is protected with Fmoc at the alphaamino group and activated at its carboxylic acid group with the PyBOP.

The arginine residues which were coupled in order to produce the hexapeptide of the structure mentioned at the beginning of the present example, were furthermore protected in their guanidino side chain with the 2,2,5,7,8-pentamethyl-chromane-6-sulfonyl, which is abbreviated as Pmc.

The last amino acid which was coupled to the sequence of the remaining amino acids for the preparation of the polypeptide, i.e. the hexapeptide mentioned before, was the inventive new tryptophan derivative which was prepared according to the process of example 4. Before performing the coupling reaction also the free carboxylic acid group of said tryptophan derivative was activated with PyBOP.

After the finishing of the synthesis of the amino acid sequence of said hexapeptide, in a single reaction step there was performed the splitting off of the sulfonyl containing side chain protective group of the totally four arginine moieties of said hexapeptide structure as well as also the splitting off of the Boc-protective group of the NH-group of the indole residue of the tryptophan moiety, and furthermore also the splitting off of the produced hexapeptide from the resin. During said step of performing the above mentioned splitting off reactions, however, the protective group for the alphaamino group of the tryptophan, i.e. the Fmoc-protective group remains so that the hexapeptide with the N-terminal, protected with Fmoc having the structure stated at the beginning of the present example, was recovered.

The simultaneous splitting off of the mentioned sulfonyl containing protective groups of the four arginine moieties, of the NH-protective group of the indole nucleus of the tryptophan moiety and of the hexapeptide from the resin, was performed by treating the resin with a mixture of 75% by weight of trifluoroacetic acid plus 20% by weight of ethane-dithiol plus 5% by weight of water, and said treatment was performed for two hours.

Tests which were performed with the high pressure liquid chromatography (hplc) showed that said single step cleavage operation was performed with a yield of more than 95%. Accordingly, the loss of yield due to a sulfonation of the tryptophan moiety of said hexapeptide was less than 5%.

Example for Comparison

The preparation of the hexapeptide described in example 5 was performed in an analogous way, except however that the tryptophan moiety was introduced as tryptophan derivative which is protected at the alphaamino group with Fmoc, in which however the NH-group of the indole nucleus was present as free, unprotected NH-group. The activation of the carboxylic group of said tryptophan derivative was performed as described in example 5, i.e. with PyBOP.

The simultaneous splitting off of the sulfonyl containing side chain protective group of the arginine moiety and of the prepared hexapeptide from the resin, was perfomred in an analogous way as described in example 5, and the resulting final product was analyzed as described in example 5, i.e. by performing a hplc.

According to said example for comparison, however, the cleaving reaction gave only a 60% yield of the corresponding hexapeptide, because 40% of the tryptophan moieties were destroyed during said splitting off reaction through a sulfonation.

Comparing the results of example 5 and the results of the present example for comparison, accordingly, the unexpected advantages which are achieved by using the new inventive tryptophan derivatives for performing a peptide synthesis, are clearly evident.

What is claimed is:

1. A protected derivative of tryptophan comprising a tryptophan moiety having a protected α-amino group and an optionally modified carboxylic acid group, wherein
   the NH-group of the tryptophan indole nucleus is protected with a tert.-butyloxycarbonyl group,
   the tryptophan α-amino group is protected with a 9-fluorenyl-methyloxy-carbonyl group, and
   the optionally modified carboxylic acid group is
   (i) present as a free COOH group,
   (ii) modified with a protecting group,
   (iii) modified with an activating group, or
   (iv) comprises an acyl group bonded to a moiety other than a protecting group or an activating group.

2. A protected tryptophan derivative according to claim 1 wherein the optionally modified carboxylic acid group comprises an acyl group bonded to
   a polymeric material,
   an amino group of another amino acid,
   an amino group of dipeptide,
   an amino group of a polypeptide, or
   an amino group of a protein.

3. A protected tryptophan derivative according to claim 1 wherein the optionally modified carboxylic acid group comprises a carboxylic acid group modified with the activating group benzo-triazole-1-yl-oxy-tris-pyrrolidino-phosphoniumhexafluorophosphate.

4. A protected tryptophan derivative according to claim 2 wherein the optionally modified carboxylic acid group comprises a carboxylic acid group bound to the linker of a resin.

5. A protected tryptophan derivative according to claim 2 wherein the optionally modified carboxylic acid group comprises an acyl group bonded to an α-amino group of a dipeptide, polypeptide, or protein containing at least one arginine moiety having an optionally protected guanidino group.

6. A protected tryptophan derivative according to claim 5 wherein the guanidino group of the arginine moiety is protected by a sulfonyl-containing group.

7. A protected tryptophan derivative according to claim 6 wherein the sulfonyl-containing group is methoxytrimethyl-sulfonyl or 2,2,5,7,8-pentamethyl-chroman-6-sulfonyl.

* * * * *